United States Patent
Honda et al.

(10) Patent No.: US 7,279,607 B2
(45) Date of Patent: Oct. 9, 2007

(54) PROCESS FOR PRODUCING ANTHRACENE DIETHER

(75) Inventors: Hiroyuki Honda, Kanagawa (JP); Hiroki Nakano, Kanagawa (JP); Shigeaki Numata, Kanagawa (JP)

(73) Assignee: Kawasaki Kasei Chemicals Ltd., Kawasaki-shi (JP)

( * ) Notice: Subject to any disclaimer, the term of this patent is extended or adjusted under 35 U.S.C. 154(b) by 0 days.

(21) Appl. No.: 10/539,807

(22) PCT Filed: Dec. 19, 2002

(86) PCT No.: PCT/JP02/13314

§ 371 (c)(1), (2), (4) Date: Jun. 20, 2005

(87) PCT Pub. No.: WO2004/056734

PCT Pub. Date: Jul. 8, 2004

(65) Prior Publication Data

US 2006/0079721 A1 Apr. 13, 2006

(51) Int. Cl.
*C07C 43/20* (2006.01)

(52) U.S. Cl. ...................................... 568/633

(58) Field of Classification Search ................. 568/633
See application file for complete search history.

(56) References Cited

FOREIGN PATENT DOCUMENTS

JP 2000-344704 12/2000

OTHER PUBLICATIONS

Seitz et al. Synthesis, 1986, p. 686-688.*
John McMurry Organic Chemistry $2^{nd}$ edition, p. 343-344, and 355.*
Ulrich Seitz et al.: "Phasen-Transfer-Katalyse unter reduzierenden Bedingungen: Hydrochinon-dialkylether aus Chinonen" SYNTHESIS, pp. 686-688, Aug. 1986.

* cited by examiner

*Primary Examiner*—Rebecca Anderson
*Assistant Examiner*—Yong Chu
(74) *Attorney, Agent, or Firm*—Oblon, Spivak, McClelland, Maier & Neustadt, P.C.

(57) ABSTRACT

An industrially advantageous process is presented whereby a high purity anthracene diether can be produced in good yield.

An aqueous medium containing an alkali salt of 9,10-anthracenediol is added to an organic solvent containing an etherifying agent in the presence or absence of a quaternary ammonium compound or a quaternary phosphonium compound, to carry out the etherifying reaction to produce the anthracene diether.

8 Claims, No Drawings

PROCESS FOR PRODUCING ANTHRACENE DIETHER

TECHNICAL FIELD

The present invention relates to a process for producing an anthracene diether. More particularly, it relates to a process for producing a dialkoxyanthracene useful as a sensitizer for a photocurable composition employing energy rays such as ultraviolet rays as the light source, particularly a dialkoxyanthracene such as 9,10-dipropoxyanthracene or 9,10-dibutoxyanthracene, or a diaryloxyanthracene such as 9,10-diphenoxyanthracene.

BACKGROUND ART

Heretofore, as a process for producing a 9,10-dialkoxyanthracene, a process is, for example, known wherein an anthracenedione compound is reduced and alkylated as disclosed in U. Seitz et al., Synthesis, 686-688 (1986). The process disclosed in this publication is a process wherein in a two phase solvent system having water and methylene chloride mixed, hydrosulfite is used as a reducing agent, and methyl iodide is used as an alkylating agent. However, the process disclosed in this publication has a problem of environmental pollution by methylene chloride, and further it can hardly be regarded as an industrially advantageous process, as an expensive alkylating agent is employed.

Further, JP-A-2000-119208 discloses a process wherein an anthracenedione compound is reduced and alkylated in an alcohol medium by using hydrosulfite as a reducing agent and diethyl acetate as an alkylating agent. However, according to the test conducted by the present inventors, if dipropyl sulfate or propyl bromide was used as an alkylating agent when dipropoxy anthracene was prepared by the process disclosed in this publication, by-products were substantial, and the desired dipropoxyanthracene was not obtained. Further, in a case where butyl bromide was used as an alkylating agent, dibutoxyanthracene could not be obtained.

Under such a circumstance, the present inventors have conducted an extensive study for the purpose of providing a process for producing, industrially advantageously in good yield, a dialkoxyanthracene, particularly a high purity anthracene diether such as 9,10-dipropoxyanthracene or 9,10-dibutoxyanthracene, and as a result, the present invention has been accomplished.

DISCLOSURE OF THE INVENTION

To solve the above-mentioned problems, the present inventors have conducted an extensive study and as a result, have arrived at the present invention having the following constructions.

(1) A process for producing an anthracene diether represented by the following formula (1):

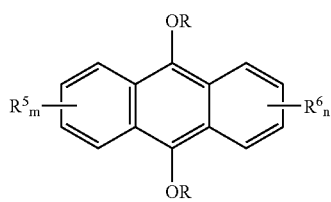

(wherein R is an alkyl group, an allyl group, an aryl group, a benzyl group, a hydroxyalkyl group or an alkoxyalkyl group, each of $R^5$ and $R^6$ is a substituent inert to etherification, and each of m and n is an integer of from 0 to 4), which comprises reacting an etherifying agent and an alkali salt of a 9,10-anthracenediol compound to produce the anthracene diether, characterized in that an aqueous medium containing the alkali salt of a 9,10-anthracenediol compound is added to an organic solvent containing the etherifying agent to carry out the reaction.

(2) The process for producing an anthracene diether according to the above (1), wherein the etherifying agent is one selected from dialkyl sulfates, alkyl halides, aryl halides or allyl halides.

(3) The process for producing an anthracene diether according to the above (1) or (2), wherein the organic solvent is one selected from polar solvents.

(4) The process for producing an anthracene diether according to the above (3), wherein the polar solvents are those selected from aprotic polar solvents.

(5) A process for producing an anthracene diether represented by the following formula (1):

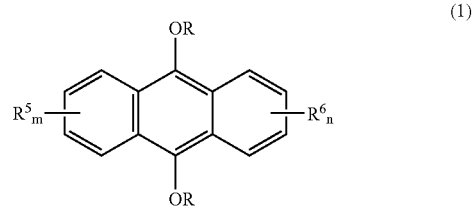

(wherein R is an alkyl group, an allyl group, an aryl group, a benzyl group, a hydroxyalkyl group or an alkoxyalkyl group, each of $R^5$ and $R^6$ is a substituent inert to etherification, and each of m and n is an integer of from 0 to 4), which comprises reacting an etherifying agent and an alkali salt of a 9,10-anthracenediol compound to produce the anthracene diether, characterized in that an aqueous medium containing the alkali salt of a 9,10-anthracenediol compound and an organic solvent containing the etherifying agent are mixed in the presence of a quaternary ammonium compound or a quaternary phosphonium compound to carry out the reaction.

(6) The process for producing an anthracene diether according to the above (5), wherein the aqueous medium containing the alkali salt of a 9,10-anthracenediol compound is added to the organic solvent containing the etherifying agent to carry out the reaction.

(7) A process for producing an anthracene diether represented by the following formula (1):

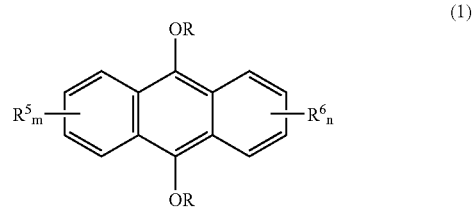

(wherein R is an alkyl group, an allyl group, an aryl group, a benzyl group, a hydroxyalkyl group or an alkoxyalkyl group, each of $R^5$ and $R^6$ is a substituent inert to etherification, and each of m and n is an integer of from 0 to 4), which comprises reacting an etherifying agent and an alkali salt of a 9,10-anthracenediol compound to produce the anthracene diether, characterized in that an aqueous medium containing the alkali salt of a 9,10-anthracenediol compound is added to an alkyl halide in the presence of a quaternary ammonium compound or a quaternary phosphonium compound to carry out the reaction.

(8) The process according to the above (5), (6) or (7), wherein as the quaternary ammonium compound or the quaternary phosphonium compound, a quaternary ammonium compound or a quaternary phosphonium compound represented by the following formula (4):

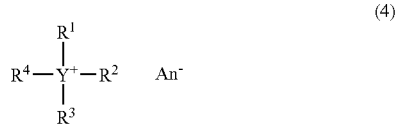

(4)

(wherein each of $R^1$ to $R^4$ which are independent of one another, is a low molecular weight or high molecular weight organic group, particularly a substituted or unsubstituted alkyl, cycloalkyl or aryl group, Y is a nitrogen atom or a phosphorus atom, and $An^-$ is an anion) is used.

EMBODIMENTS OF THE INVENTION

The first embodiment of the present invention is a process wherein an aqueous medium containing an alkali salt of a 9,10-anthracenediol compound is added to an organic solvent containing an etherifying agent to carry out the reaction.

The 9,10-anthracenediol compound is represented by the following formula (2):

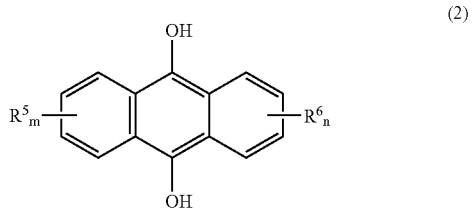

(2)

(wherein like in the above formula (1), each of $R^5$ and $R^6$ is a substituent inert to etherification, and each of m and n is an integer of from 0 to 4) and can be obtained by reducing the corresponding 9,10-anthracenedione compound.

Each of substituents $R^5$ and $R^6$ is a substituent inert to the etherification reaction in the process of the present invention. Specifically, a $C_{1-10}$ alkyl group, an alkenyl group, an alkoxy group, an amino group, an alkylamino group, an alkylsulfonyl group, an alkoxycarbonyl group or a halogen group, may, for example, be mentioned. Each of m and n represents the number of substituents bonded to the aromatic ring and is an integer of from 0 to 4, preferably an integer of from 0 to 2.

In an aqueous medium containing an alkaline active agent, the 9,10-anthracenediol compound is dissolved in the form of an alkali salt of a 9,10-anthracenediol compound represented by the formula (3):

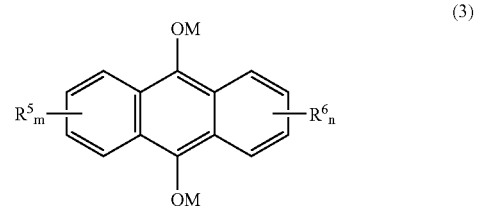

(3)

(wherein $R^5$, $R^6$, m and n have the same meanings as in the above formula (2), and M is an alkali metal). As such an alkaline active agent, sodium hydroxide or potassium hydroxide may, for example, be mentioned, and it is used in an amount of preferably at least 2 times by mol, more preferably from 2.2 to 3 times by mol, relative to the 9,10-anthracenediol compound. The aqueous medium means, in addition to water, a lower alcohol such as methyl alcohol, ethyl alcohol or isopropyl alcohol or a mixed medium of such a lower alcohol with water, or a water-soluble ether such as tetrahydrofuran or dioxane or a mixed medium of such a water-soluble lower ether with water. The solubility of the alkali salt of a 9,10-anthracenediol compound varies depending upon the types of the substituents, but in the case of an aqueous solution, a solution having a concentration of from about 5 to 30 wt % is preferably selected.

As the method for reducing the 9,10-anthracenedione compound, (1) a method of carrying out hydrogen reduction in a solvent such as an alcohol in the presence of a hydrogenation catalyst, or (2) a method of carrying out reduction in an aqueous medium by means of hydrosulfite, may, for example, be mentioned. The above method (2) is preferred, since by the reduction in the presence of an alkaline compound such as sodium hydroxide, an alkali salt of a 9,10-anthracenediol compound can directly be obtained. Further, (3) a method for producing an alkali salt of anthracenediol which comprises reducing 9,10-anthracenedione with a solution of an alkaline compound of 1,4-dihydro-9,10-dihydroxyanthracene (JP-A-9-16982) may, for example, be mentioned. This method (3) is preferred, since 1,4-dihydro-9,10-dihydroxyanthracene used for the reduction, becomes anthracene diol, whereby there will be no necessity to remove the reducing agent after use.

The etherification agent in the present invention may, for example, be an alkylating agent, an aryl-modifying agent or an allyl-modifying agent, which will be described below. Namely, the alkylating agent may, for example, be a dialkyl sulfate such as diethyl sulfate or dipropyl sulfate, or an alkyl halide such as ethyl bromide, propyl bromide or butyl bromide. The aryl-modifying agent may, for example, be an aryl halide such as bromobenzene, chlorobenzene, p-chlorotoluene, p-bromotoluene, m-bromotoluene, m-chlorotoluene, α-chloronaphthalene, α-bromonaphthalene, β-chloronaphthalene or β-bromonaphthalene. Further, the allyl-modifying agent may, for example, be an allyl halide such as allyl bromide, allyl chloride or methallyl chloride. As other etherifying agents, 2-bromoethanol may be mentioned for hydroxyethylation, and 2-bromoethylmethyl ether may be mentioned for methoxyethyllation.

Among these etherifying agents, from the viewpoint of the reactivity, etc., preferred is a dialkyl sulfate, an alkyl halide, an aryl halide or an allyl halide, and particularly preferred is an alkyl halide such as propyl bromide or butyl bromide. Such an etherifying agent is used in an amount of at least 2 times by mol, particularly preferably within a range of from 2 to 5 times by mol, relative to the alkali metal of a 9,10-anthracenediol compound as the material. If it is less than 2 times by mol, an unreacted case will increase, and if it exceeds 5 times by mol, side reactions will increase, such being undesirable.

In the present invention, the organic solvent to contain such an etherification agent may be any solvent, so long as it is a solvent capable of constantly dissolving the etherification agent, but a polar solvent is particularly preferred. The polar solvent may be an aprotic polar solvent or a protic polar solvent, but an aprotic polar solvent is more preferred.

As the aprotic polar solvent, the following may be mentioned. Namely, an N,N-di-$C_{1-2}$-alkylamide of a $C_{1-3}$-carboxylic acid, such as N,N-dimethylformamide, N,N-diethylformamide, N,N-dipropylformamide, N,N-dimethylacetamide, N,N-diethylacetamide, N,N-dipropylacetamide or N,N-dimethylpropionic amide; a cyclic N-alkyl carboxylic amide such as N-methylpyrrolidone; a cyclic N-formyl compound such as N-formylpholine or N-formylpiperidine; a hexaalkylphosphoric triamide such as hexamethyl phosphoric triamide; a sulfoxide such as dimethylsulfoxide or tetramethylene sulfoxide; a tetraalkylurea such as tetramethylurea; a cyclic ether such as tetrahydrofuran, 1,4-dioxane or trioxane; an acetal such as 1,2-dimethoxyethane, 1,2-dibutoxyethane, diethylene glycol dimethyl ether, diethylene glycol diethyl ether or diethylene glycol dibutyl ether; a ketone such as acetone, methyl ethyl ketone, 2-pentanone, 3-pentanone, 2-hexanone, methyl isobutyl ketone, 2-heptanone, 4-heptanone, diisobutyl ketone or acetonitrile acetone; or an ether such as diethyl ether, dipropyl ether, diisopropyl ether or dibutyl ether, may be mentioned.

On the other hand, as the protic polar solvent, the following may be mentioned. Namely, an alcohol such as methanol, ethanol, 1-propanol, 2-propanol, 1-butanol, 2-butanol or tert-butyl alcohol; or a glycol such as ethylene glycol, propylene glycol, trimethylene glycol, 1,2-butandiol, 1,3-butandiol or 1,4-butandiol, may be mentioned.

Among these polar solvents, particularly preferred is an aprotic polar solvent having a boiling point of at least 60° C., such as N-methylpyrrolidone, N,N-dimethylformamide, methyl ethyl ketone or methyl isobutyl ketone.

Such an organic solvent is used usually in an amount of from 1.5 to 10 times by weight relative to the alkali salt of a 9,10-anthracenediol compound as the material.

In the first embodiment for producing an anthracene diether of the present invention, an aqueous medium containing the alkali salt of a 9,10-anthracenediol compound is added to the organic solvent containing the etherifying agent to carry out the etherifying reaction to obtain the anthracene diether as the desired substance. In order to let the etherification reaction proceed efficiently, the order of addition of these materials is important. Namely, if the order of addition is changed, and the organic solvent containing the etherifying agent is added to the aqueous solution of the alkali salt of a 9,10-anthracenediol compound, side reactions tend to proceed, whereby the yield of the desired anthracene diether will decrease, such being undesirable.

The temperature for the etherification reaction in the present invention is preferably at least 0° C. where the aqueous solution of the alkali salt of a 9,10-anthracenediol compound will not freeze and not higher than the boiling point of the etherifying agent dissolved in the solvent, under atmospheric pressure. If the temperature is lower than 20° C., the etherification reaction tends to hardly proceed, and if it exceeds 80° C., side reactions tend to proceed. Accordingly, it is preferred to select the temperature within a range of from 20 to 80° C.

The second embodiment for producing an anthracene diether of the present invention is a process wherein an aqueous medium containing the alkali salt of a 9,10-anthracenediol compound and an organic solvent containing the etherifying agent are mixed to carry out the reaction, and wherein the reaction is carried out in the presence of a quaternary ammonium compound or a quaternary phosphonium compound.

The quaternary ammonium compound or the quaternary phosphonium compound preferred for this reaction is a quaternary ammonium compound or a quaternary phosphonium compound represented by the following formula (4):

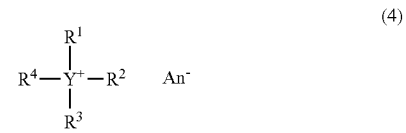

(wherein each of $R^1$ to $R^4$ which are independent of one another, is a low molecular weight or high molecular weight organic group, particularly a substituted or unsubstituted alkyl, cycloalkyl or aryl group, Y is a nitrogen atom or a phosphorus atom, and $An^-$ is an anion).

A particularly preferred compound is a quaternary ammonium compound of the above formula wherein Y=N, and each of $R^1$, $R^2$ and $R^3$ which are independent of one another, is a $C_{1-18}$ alkyl group and $R^4$ is a $C_{1-18}$ alkyl group or a phenyl group.

A suitable alkyl group may, for example, be a $C_{1-18}$ alkyl group such as a methyl group, an ethyl group, a propyl group, a n-butyl group, a hexyl group, an octyl group, a dodecyl group or an octadecyl group, or a $C_{1-18}$ alkyl group substituted by a hydroxyl group, a cyano group or a phenyl group, such as a 2-hydroxyethyl group, a 2-hydroxypropyl group, a 2-cyanoethyl group or a 2-phenylethyl group. A suitable cycloalkyl group for each of $R^1$ to $R^4$ may, for example, be a $C_{5-6}$ cycloalkyl group such as a cyclopentyl group or a cyclohexyl group, and a phenyl group substituted by a $C_{1-4}$ alkyl group. The anion $An^-$ may preferably be a halogen ion, particularly a chlorine ion or a bromine ion, or a hydrogen sulfate ion.

As the quaternary ammonium compound which may be used in the present invention, the following may, for example, be mentioned. Tetrabutylammonium bromide or chloride, dodecyltrimethylammonium chloride, n-hexadecyltributylammonium chloride, tetrapropylammonium chloride, benzyltriethylammonium chloride, benzyltributylammonium bromide, benzyltrihexylammonium bromide, benzyltrioctylammonium bromide, tetrabutylammonium iodide, trioctylmethylammonium chloride, N-dodecylpyridinium bromide, cyclohexyltriethylammonium bromide, n-dodecyltriethylammonium bromide, n-octyltributylammonium bromide, n-hexadecyltrimethylammonium bromide, n-hexadecyltriethylammonium bromide, n-hexadecyltripropylammonium bromide, n-dodecyl-bis-(β-hydroxyethyl)-benzylammonium chloride and n-hexadecyl-tri(β-hydroxyethyl)-ammonium chloride. A suitable phosphonium salt may, for example, be n-hexadecyltributylphosphonium bromide, tetrabutylphosphonium chloride, tetraphenylphosphonium bromide or trioctylethylphosphonium bromide. Among them, particularly preferred is tetrabutylammonium bromide or tetrabutylammonium chloride, n-hexadecyltributylammonium chloride, tetrapropylammonium chloride, benzyltributylammonium bromide or chloride, or trioctylmethylammonium bromide or chloride.

The amount of the quaternary ammonium compound or the quaternary phosphonium compound to be used in the present invention may be varied within a wide range, but it is preferably from 0.001 to 10 times by mol, particularly preferably from 0.01 to 1 time by mol, per mol of the alkali salt of a 9,10-anthracenediol compound. It is undesirable to use it excessively, since such is economically disadvantageous.

As the method of carrying out the reaction in the presence of the quaternary ammonium compound or the quaternary phosphonium compound, a method may, for example, be mentioned wherein the quaternary ammonium compound or the quaternary phosphonium compound is added to the organic solvent containing the etherifying agent and then mixed with the aqueous medium wherein the alkali salt of a 9,10-anthracenediol compound is dissolved, to carry out the reaction. The order of mixing the respective reactants in the present invention may be any order, but a method is preferred wherein the quaternary ammonium compound or the quaternary phosphonium compound is added in a prescribed amount to the organic solvent containing the etherifying agent, and then, the aqueous medium wherein the alkali salt of a 9,10-anthracenediol compound, is dissolved, is added. By this method of employing the quaternary ammonium compound or the quaternary phosphonium compound, a preferred effect may be obtained such that the etherification reaction proceeds quickly, and formation of by-products can be suppressed. Especially in a case where an organic solvent poor in miscibility with water is used, if the etherification reaction is carried out in the presence of a phase transfer catalyst such as tetrabutylammonium bromide, the etherification reaction product will be extracted in the organic solvent, whereby separation of the reaction product will be easy, and such may be regarded as an industrially preferred method. Such an organic solvent poor in miscibility with water may, for example, be an aliphatic hydrocarbon type organic solvent such as n-hexane or cyclohexane, an aromatic hydrocarbon type organic solvent such as benzene, toluene or xylene, or a halogenated hydrocarbon type organic solvent such as chloroform or dichloromethane.

Further, as the third embodiment for producing an anthracene diether of the present invention, a method may be mentioned wherein in a case where a certain specific etherification agent is employed, the reaction is carried out without using any organic solvent. Namely, it is a process for producing an anthracene diether wherein an alkyl halide or the like is used as the etherifying agent, and the etherifying reaction is carried out by adding an aqueous medium containing the alkali salt of a 9,10-anthracenediol compound to the alkyl halide in the presence of the quaternary ammonium compound or the quaternary phosphonium compound without using any organic solvent. For example, a process may be mentioned wherein using an alkyl bromide such as butyl bromide in excess, an aqueous medium containing the alkali salt of a 9,10-anthracenediol compound, is added in the presence of the quaternary ammonium compound or the quaternary phosphonium compound, to carry out the reaction.

According to the process of the present invention, an anthracene diether can be obtained which is represented by the following formula:

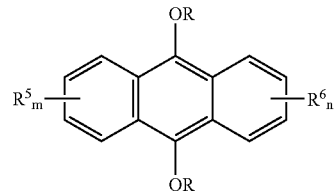

(1)

(wherein R is an alkyl group, an allyl group, an aryl group, a benzyl group, a hydroxyalkyl group or an alkoxyalkyl group, and each of $R^5$ and $R^6$ is a substituent inert to etherification, and each of m and n is an integer of from 0 to 4). The alkyl group for substituent R may be a $C_{1-5}$ alkyl group, preferably a $C_{1-4}$ alkyl group. Specifically, a methyl group, an ethyl group, a n-propyl group, an i-propyl group, a n-butyl group, an i-butyl group, a t-butyl group, a n-pentyl group or an i-pentyl group may, for example, be mentioned. The allyl group may, for example, be allyl or 2-methylallyl. The aryl group may, for example, be a phenyl group, an o-tolyl group, a m-tolyl group, a p-tolyl group, a naphthyl group or a biphenyl group.

The hydroxyalkyl group may, for example, be a 2-hydroxyethyl group, a 3-hydroxypropyl group, a 2-methyl-2-hydroxyethyl group or a 2-ethyl-2-hydroxyethyl group. The alkoxyalkyl group may, for example, be a 2-methoxyethyl group, a 3-methoxypropyl group, a 2-ethoxyethyl group or a 3-ethoxypropyl group.

Each of substituents $R^5$ and $R^6$ is a substituent inert to the etherification reaction in the process of the present invention, and specifically, a $C_{1-10}$ alkyl group, an alkenyl group, an alkoxy group, an amino group, an alkylamino group, an alkylsulfonyl group, an alkoxycarbonyl group or a halogen atom, may, for example, be mentioned.

A specific example of the anthracene diether represented by the above formula (1) to be produced in the present invention may, for example, be a dialkoxyanthracene such as 9,10-dimethoxyanthracene, 9,10-diethoxyanthracene, 9,10-dipropoxyanthracene, 9,10-dibutoxyanthracene, 2-ethyl-9,10-diethoxyanthracene, 2-(4-methylpentyl)-9,10-diethoxyanthracene, 2-(4-methyl-3-pentenyl)-9,10-diethoxyanthracene or 2,3-diethyl-9,10-diethoxyanthracene; a diaryloxyanthracene such as 9,10-diphenoxyanthracene, 9,10-di(p-tolyloxy)anthracene or 9,10-dinaphthyloxyanthracene; a diallyloxyanthracene such as 9,10-diaryloxyanthracene or 9,10-di(2-methylallyloxy)anthracene; 9,10-di(2-hydroxyethoxy)anthracene; or 9,10-di(2-methoxyethoxy)anthracene.

The anthracene diether represented by the above formula (1), particularly a dialkoxyanthracene, obtained by the process of the present invention, is useful as a sensitizer for a photocurable composition employing energy rays such as ultraviolet rays as the light source.

EXAMPLES

Now, the present invention will be described in detail with reference to Examples. However, it should be understood that the present invention is by no means restricted by the following Examples. In the following Examples, "%" means "wt %" unless otherwise specified.

Example 1

A three necked flask having a capacity of 300 ml and equipped with a stirrer, a thermometer, a heating jacket and a charge inlet, 32 g of a 30% sodium hydroxide aqueous solution and 57 g of water were charged, and with stirring, 25 g of 9,10-anthracenedione was charged and suspended, whereupon air in the flask was substituted by nitrogen. While stirring the content in this flask, 130 g of an aqueous solution of a sodium salt of 1,4-dihydro-9,10-dihydroxyanthracene (22% as the concentration of anthracenedione) was added, and the mixture was maintained at an internal temperature within a range of from 85 to 90° C. for 4 hours to obtain an aqueous solution of a sodium salt of 9,10-anthracenediol.

Into an autoclave having a capacity of 1 L and equipped with a stirrer, a thermometer, a heating jacket and a charge inlet, a solution having 92 g of propyl bromide (1-bromopropane, the same applies hereinafter) dissolved in 300 g of dimethylformamide, was charged, and the internal temperature was raised to 65° C. and maintained at that level. To this autoclave, the aqueous solution of the sodium salt of 9,10-anthracenediol prepared by the above method, was added over a period of one hour with stirring. After completion of the addition of the aqueous solution of the sodium salt of 9,10-anthracenediol, the internal temperature was raised to and maintained at 70° C. for one hour. Then, the internal temperature was lowered to 30° C. to have crystals of the product precipitated. The crystals were collected by filtration, washed with 100 ml of methanol and dried to obtain a product. The product had a melting point of 93° C. and was confirmed to be 9,10-dipropoxyanthracene by the NMR spectrum. The amount of the product was 48 g, and the yield based on the sodium salt of 9,10-anthracenediol (hereinafter referred to simply as the yield) was 60 mol %.

Comparative Example 1

Firstly, by the method disclosed in Example 1, an aqueous solution of the sodium salt of 9,10-anthracenediol was prepared. Then, into the autoclave used in the method disclosed in Example 1, this aqueous solution of the sodium salt of 9,10-anthracenediol was charged, and the internal temperature was raised to and maintained at 65° C. with stirring. A solution having 92 g of propyl bromide dissolved in 300 g of dimethylformamide, was added over a period of one hour. After completion of the addition of propyl bromide, the internal temperature was further raised to and maintained at 70° C. for one hour. Then, the internal temperature was lowered to 30° C. to have crystals precipitated, followed by filtration and drying in the same manner as in Example 1 to obtain a product. However, in the NMR spectrum, the product could not be confirmed to be 9,10-dipropoxyanthracene, and the melting point was also 171° C. The structure assumed from the NMR was 9-hydro-9-oxo-10-hydroxy-10-propylanthracene.

Example 2

Firstly, by the method disclosed in Example 1, an aqueous solution of the sodium salt of 9,10-anthracenediol was prepared. Then, into the autoclave used in the method disclosed in Example 1, a solution having 108 g of butyl bromide (1-bromobutane, the same applies hereinafter) dissolved in 300 g of dimethylformamide, was charged, and the internal temperature was raised to and maintained at 65° C. To this autoclave, the aqueous solution of the sodium salt of 9,10-anthracenediol prepared by the method disclosed in Example 1, was added over a period of one hour with stirring. After adding the aqueous solution of the sodium salt of 9,10-anthracenediol, the internal temperature was further raised to and maintained at 70° C. for one hour with stirring. Then, the internal temperature was lowered to 30° C. to have crystals of the product precipitated. The crystals were collected by filtration, washed with methanol and dried to obtain a product. the product had a melting point of 107° C., and was confirmed to be 9,10-dibutoxyanthracene by the NMR spectrum. The amount of the product was 59 g, and the yield was 70 mol %.

Comparative Example 2

Firstly, by the method disclosed in Example 1, an aqueous solution of the sodium salt of 9,10-anthracenediol was prepared. Then, into the autoclave used in the method disclosed in Example 1, this aqueous solution of the sodium salt of 9,10-anthracenediol was charged, and the internal temperature was raised to and maintained at 65° C. with stirring. A solution having 108 g of butyl bromide dissolved in 300 g of dimethylformamide, was added over a period of one hour. After completion of the addition of butyl bromide, the internal temperature was further raised to and maintained at 70° C. for one hour. Then, the internal temperature was lowered to 30° C. to have crystals precipitated, followed by filtration and drying in the same manner as in Example 1 to obtain a product. However, the product was a mixture of 9,10-dibutoxyanthracene, 9,10-anthracenedione and 9-hydro-9-oxo-10-butylanthracene having the structure assumed by NMR. The purity of 9,10-dibutoxyanthracene in the product was calculated, whereby the yield was 9 mol %.

Example 3

In a three necked flask having a capacity of 500 ml and equipped with a stirrer, a thermometer, a heating jacket and a charge inlet, 16 g of sodium hydroxide was dissolved in 80 g of water, and 40 g of 9,10-anthracenedione was charged and suspended with stirring, whereupon air in the flask was substituted by nitrogen. While stirring the content in this flask, 209 g of an aqueous solution of a sodium salt of 1,4-dihydro-9,10-dihydroxyanthracene (22% as the concentration of anthracenedione) was added, and the internal temperature was maintained within a range of from 95 to 97° C. for 4 hours to obtain an aqueous solution of the sodium salt of 9,10-anthracenediol.

Into an autoclave having a capacity of 300 ml and equipped with a stirrer, a thermometer, a heating jacket and a charge inlet, a solution having 40 g of butyl bromide and 1.9 g of tetrabutylammonium bromide dissolved in 70 g of methyl ethyl ketone, was charged, and the internal temperature was raised to and maintained at 65° C. To this autoclave, 100 g of the aqueous solution of the sodium salt of 9,10-anthracenediol prepared by the above-mentioned method, was added over a period of 3 hours with stirring. After completion of the addition of the aqueous solution of the sodium salt of 9,10-anthracenediol, the internal temperature was further raised to and maintained at 70° C. for one hour. Then, the internal temperature was lowered to 30° C., and 50 ml of methanol was added to the autoclave to have crystals of the product precipitated. The crystals were collected by filtration, washed with 100 ml of methanol and dried to obtain a product. The amount of the product was 33 g, the yield of 9,10-dibutoxyanthracene was 90 mol %.

Comparative Example 3

The same operation was carried out by the method disclosed in Example 3 except that no tetrabutylammonium bromide was added, whereby the yield of 9,10-dibutoxyanthracene was 14 mol %.

Example 4

As an addition method reverse to the method disclosed in Example 3, the same operation was carried out except that a solution having 40 g of butyl bromide dissolved in 70 g of methyl ethyl ketone, was added over a period of three hours to the aqueous solution of the sodium salt of 9,10-anthracenediol having tetrabutylammonium bromide added, whereby the yield of 9,10-dibutoxyanthracene was 70 mol %.

Example 5

The same operation was carried out by the method disclosed in Example 3 except that diethyl sulfate was used instead of butyl bromide, whereby the yield of 9,10-diethoxyanthracene was 87 mol %.

Example 6

The same operation was carried out by the method disclosed in Example 3 except that propyl bromide was used instead of butyl bromide, whereby the yield of 9,10-dipropoxyanthracene was 89 mol %.

Example 7

The same operation was carried out by the method disclosed in Example 3 except that instead of using methyl ethyl ketone as an organic solvent, butyl bromide was increased to 57 g, whereby the yield of 9,10-dibutoxyanthracene was 85 mol %.

Example 8

The same operation was carried out by the method disclosed in Example 3 except that methyl isobutyl ketone was used instead of methyl ethyl ketone, whereby the yield of 9,10-dibutoxyanthracene was 82 mol %.

Comparative Example 4

The same operation was carried out by the method disclosed in Example 3 except that isopropyl alcohol was used instead of methyl ethyl ketone, whereby the yield of 9,10-dibutoxyanthracene was 50 mol %.

Comparative Example 5

The same operation was carried out by the method disclosed in Example 3 except that o-xylene was used instead of methyl ethyl ketone, whereby the yield of 9,10-dibutoxyanthracene was 43 mol %.

INDUSTRIAL APPLICABILITY

The process of the present invention provides the following especially advantageous effects, and thus its industrial value is extremely high.

1. The desired anthracene diether can be produced industrially advantageously by using not only a dialkyl sulfate but also an industrially inexpensive alkyl halide, as an etherifying agent.

2. As compared with conventional production processes, a high purity anthracene diether can be produced in a high yield.

3. Further, by carrying out the reaction in the presence of a quaternary ammonium compound or a quaternary phosphonium compound, preferred effects can be obtained such that the etherification reaction proceeds quickly, and formation of by-products can be suppressed. Further, in the case of an alkyl halide such as butyl bromide, the reaction can be carried out without using an organic solvent.

What is claimed is:

1. A process for producing an anthracene diether represented by the following formula (1):

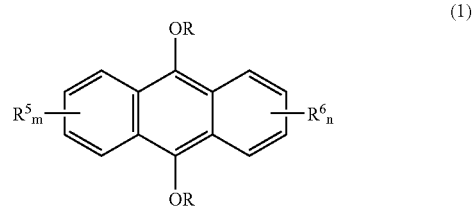

(wherein R is an alkyl group, an allyl group, an aryl group, a benzyl group, a hydroxyalkyl group or an alkoxyalkyl group, each of $R^5$ and $R^6$ is a substituent inert to etherification, and each of m and n is an integer of from 0 to 4), which comprises reacting an etherifying agent and an alkali salt of a 9,10-anthracenediol compound to produce the anthracene diether, characterized in that an aqueous medium containing the alkali salt of a 9,10-anthracenediol compound is added to an organic solvent containing the etherifying agent to carry out the reaction.

2. The process for producing an anthracene diether according to claim 1, wherein the etherifying agent is one selected from dialkyl sulfates, alkyl halides, aryl halides or allyl halides.

3. The process for producing an anthracene diether according to claim 1 or 2, wherein the organic solvent is one selected from polar solvents.

4. The process for producing an anthracene diether according to claim 3, wherein the polar solvents are those selected from aprotic polar solvents.

5. A process for producing an anthracene diether represented by the following formula (1):

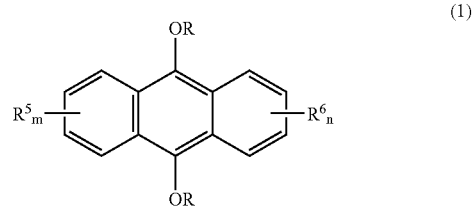

(wherein R is an alkyl group, an allyl group, an aryl group, a benzyl group, a hydroxyalkyl group or an alkoxyalkyl group, each of $R^5$ and $R^6$ is a substituent inert to etherification, and each of m and n is an integer of from 0 to 4), which comprises reacting an etherifying agent and an alkali salt of a 9,10-anthracenediol compound to produce the anthracene diether, characterized in that an aqueous medium containing the alkali salt of a 9,10-anthracenediol compound is added to an organic solvent containing the etherifying agent in the presence of a quaternary ammonium compound or a quaternary phosphonium compound to carry out the reaction.

6. The process for producing an anthracene diether according to claim 5, wherein the aqueous medium containing the alkali salt of a 9,10-anthracenediol compound is added to the organic solvent containing the etherifying agent to carry out the reaction.

7. A process for producing an anthracene diether represented by the following formula (1):

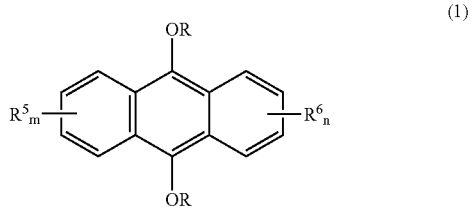

(1)

(wherein R is an alkyl group, an allyl group, an aryl group, a benzyl group, a hydroxyalkyl group or an alkoxyalkyl group, each of $R^5$ and $R^6$ is a substituent inert to etherification, and each of m and n is an integer of from 0 to 4), which comprises reacting an etherifying agent and an alkali salt of a 9,10-anthracenediol compound to produce the anthracene diether, characterized in that an aqueous medium containing the alkali salt of a 9,10-anthracenediol compound is added to an alkyl halide in the presence of a quaternary ammonium compound or a quaternary phosphonium compound to carry out the reaction.

8. The process according to claim 5, 6 or 7, wherein as the quaternary ammonium compound or the quaternary phosphonium compound, a quaternary ammonium compound or a quaternary phosphonium compound represented by the following formula (4):

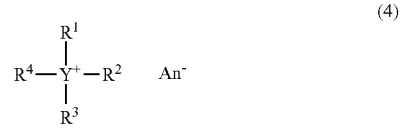

(4)

(wherein each of $R^1$ to $R^4$ which are independent of one another, is a low molecular weight or high molecular weight organic group, particularly a substituted or unsubstituted alkyl, cycloalkyl or aryl group, Y is a nitrogen atom or a phosphorus atom, and $An^-$ is an anion) is used.

* * * * *